United States Patent [19]
Buckner

[11] Patent Number: 6,090,281
[45] Date of Patent: Jul. 18, 2000

[54] BEVERAGE STORAGE AND DISPENSING CONTAINER

[76] Inventor: Lynn Buckner, P.O. Box 609, Chickamauga, Ga. 30707

[21] Appl. No.: 09/129,782

[22] Filed: Aug. 6, 1998

[51] Int. Cl.[7] .................................. C02F 1/32; C02F 1/36
[52] U.S. Cl. ...................... 210/205; 210/149; 210/175; 220/723; 222/386.5
[58] Field of Search ................................ 210/85, 175, 205, 210/103, 138, 149, 748; 222/386.5; 138/30; 220/495.01, 495.03

[56] References Cited

U.S. PATENT DOCUMENTS

| | | | |
|---|---|---|---|
| 3,122,000 | 2/1964 | Sirocky | 222/386.5 |
| 3,802,464 | 4/1974 | Frank et al. | 138/30 |
| 4,836,409 | 6/1989 | Lane | 138/30 |
| 5,068,030 | 11/1991 | Chen | 210/149 |
| 5,124,050 | 6/1992 | Ushimaru et al. | 210/748 |
| 5,389,254 | 2/1995 | Sherman | 210/138 |
| 5,531,908 | 7/1996 | Matsumoto et al. | 210/764 |
| 5,660,720 | 8/1997 | Walling | 210/85 |
| 5,686,893 | 11/1997 | Jeon | 210/103 |
| 5,766,453 | 6/1998 | Morellato et al. | 210/175 |

*Primary Examiner*—David A. Simmons
*Assistant Examiner*—Frank Lawrence
*Attorney, Agent, or Firm*—Rader, Fishman & Grauer; Ronald P. Kananen

[57] ABSTRACT

A flexible diaphragm, flexible bag or bladder tank used to store and dispense, cool or heat, and sterilize drinking water or beverages under pressure, may include at least one orifice, at least one ultraviolet sterilizing unit located within it, and at least one thermo-electric unit attached to or inserted within it.

22 Claims, 19 Drawing Sheets

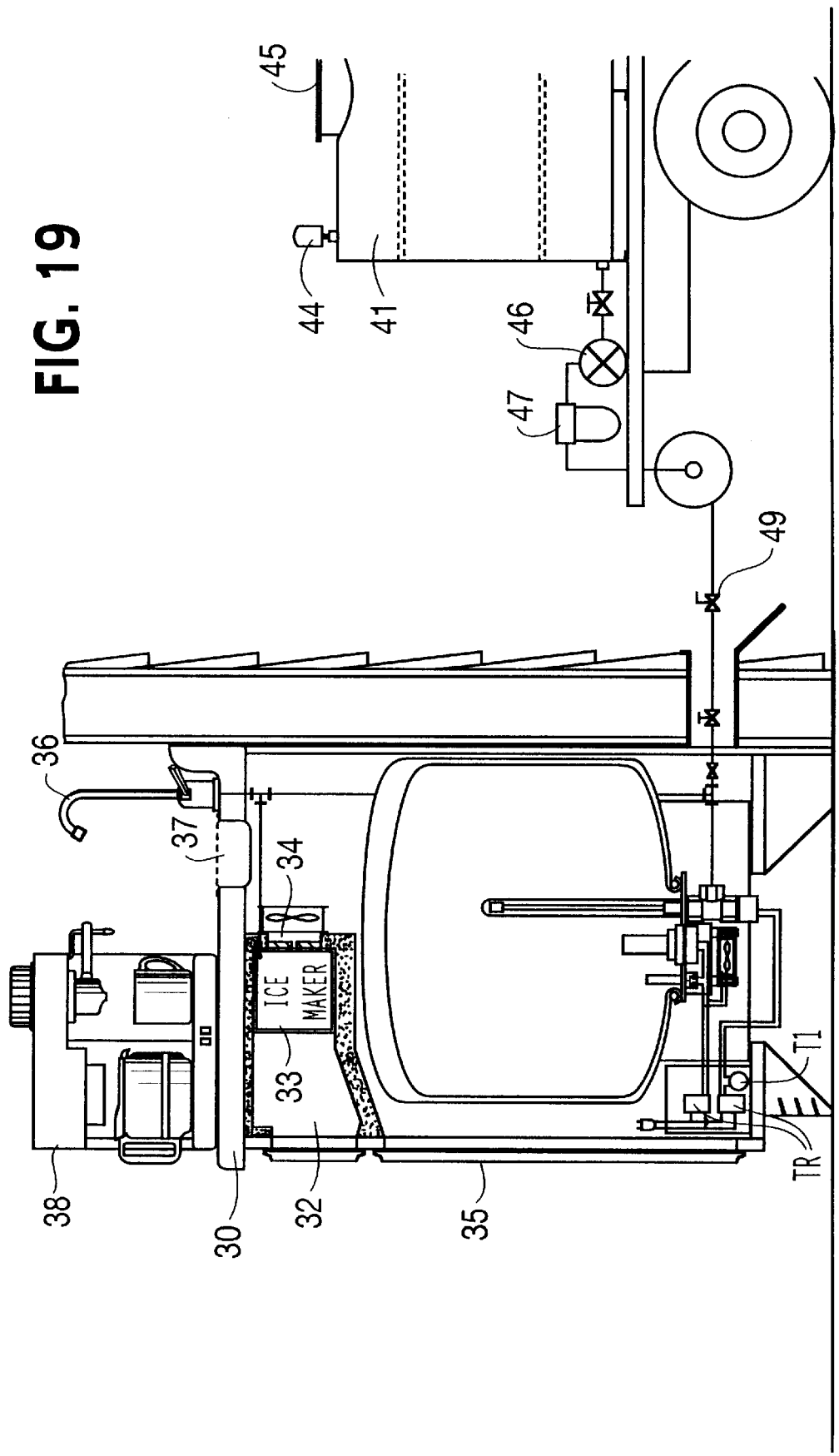

BEVERAGE STORAGE AND DISPENSING CONTAINER

BACKGROUND OF THE INVENTION

Liquids are commonly stored for extended periods of time in storage containers, and dispensed at a later time. An example is a thermos cooler, which can hold gallons of potable liquid, and thereby transport the liquid to a place where the liquid can be utilized as desired.

Perhaps the biggest problem associated with storing liquid that is later to be dispensed is contamination of the liquid over a long period of time. Large amounts of liquid will be ruined and unusable if they are contaminated by germs, bacteria, etc. before being consumed or otherwise utilized as desired.

Another problem associated with storing liquid over a long period of time is that even if the liquid is stored in an insulated environment, the liquid is subject to slight temperature adjustment toward the temperature of the surroundings of the container. Lukewarm beverages are not very desirable in general, and tend to be contaminated much faster than when they are very hot or very cold.

It is therefore an object of the present invention to provide a beverage storage and dispensing container that is able to maintain purity of the liquid that is otherwise subject to contamination.

It is another object of the present invention to provide such a container/dispenser that is able to maintain a temperature of a liquid over as long of a period of time as is desired.

It is a further object of the invention to provide such a container/dispenser that provides these benefits for as much liquid as is conceivably transportable, while at the same time, making small amounts of the stored liquid available to individuals in small portions.

It is yet another object of the invention to provide such a container/dispenser that provides all of the above benefits with easy access to further necessary power-supplied appliances and all needed serving and catering utensils and apparatuses.

SUMMARY OF THE INVENTION

The above-described needs and others are met by a liquid storage and dispensing container, which includes a tank, made of a flexible material, a liquid disperser, and a liquid sterilizer that maintains the liquid in a sterile state in the container. The liquid in the container may be any potable liquid such as drinking water or any other beverage. The sterilizer can include an ultraviolet light, an ultrasonic generator, a silver particle sterilizer, an ozone generator and injection mechanism, and other suitable sterilizing apparatuses and techniques.

At least one thermoelectric component may be attached to or contained inside the container. The liquid may be stored and dispensed under pressure, and may be cooled or heated by the thermoelectric component. If the liquid is stored under pressure, a pressure sensor may be included, which indicates a depth of or volume of the liquid in the container.

A device may be added to the container, which automatically begins and ends operation of the sterilizer. Such a device may include a timer, which provides automation of an ultraviolet light. Another device may be added, which automatically begins and ends operation of the thermoelectric device. Such a device may include a temperature sensor. The thermoelectric device may provide heat to the liquid when a switching circuit connected to the thermoelectric device is positioned in a first state, and the device may also cool the liquid when the switching circuit is positioned in a second state.

An alarm which serves as both a detector and warning device upon an event of a container malfunction and upon an event of a container defect may be added to the container. Computer hardware and software may be used to monitor and operate the alarm.

The liquid storage and dispensing container may also include an insulation layer for reducing thermal transfer between the liquid and the surroundings of the container. The container may also have a protective outer cover that surrounds the container.

Work surfaces, shelves, and storage areas may be provided in the surroundings of the container.

The above-described needs and others are also met by a method for containing and dispensing a potable liquid, which includes the steps of providing a flexible container, having at least one dispersing valve attached thereto, filling the container with the potable liquid, sterilizing the liquid in the container using a sterilizing apparatus, maintaining the liquid in the container in a sterile state using the sterilizing apparatus, cooling and heating the liquid in the container to a predetermined temperature using a thermoelectric element, and dispersing the liquid through the dispersing valve.

The method may also include the steps of pressurizing the liquid in the container, and measuring an amount of the liquid in the container using a pressure sensor. Other steps in the method may include insulating the flexible container, protecting the flexible container using a hard cover, providing work surfaces, shelves, and storage areas in the surroundings of said container, detecting an event of a container malfunction or a container defect using computer hardware and software, and alarming upon detecting a container malfunction or container defect.

The sterilizing apparatus may include an ultraviolet light, an ultrasonic generator, a silver particle sterilizer, or an ozone generator and injection mechanism. The sterilizing step may be performed automatically using a timing device. The cooling and heating step may also be performed automatically using a temperature sensing and adjusting means.

BRIEF DESCRIPTION OF THE DRAWINGS

FIG. 19 shows a liquid storage and dispensing container according to a thirteenth embodiment of the invention, which is a combination of the eleventh embodiment and the ninth embodiment.

DESCRIPTION OF THE PREFERRED EMBODIMENT

Figure 1:
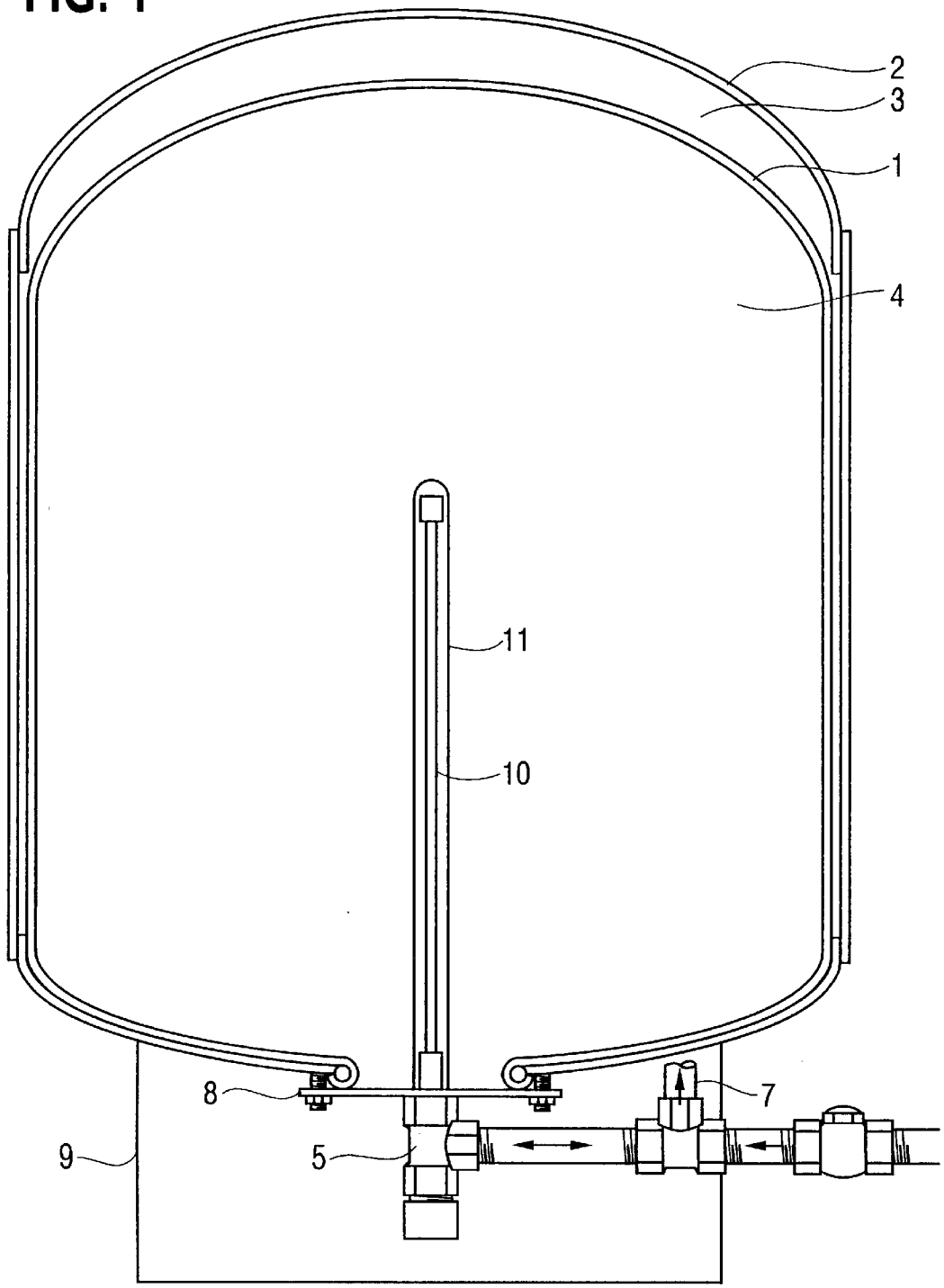
FIG. 1 shows a liquid storage and dispensing container according to a first embodiment of the invention.
Figure 2:
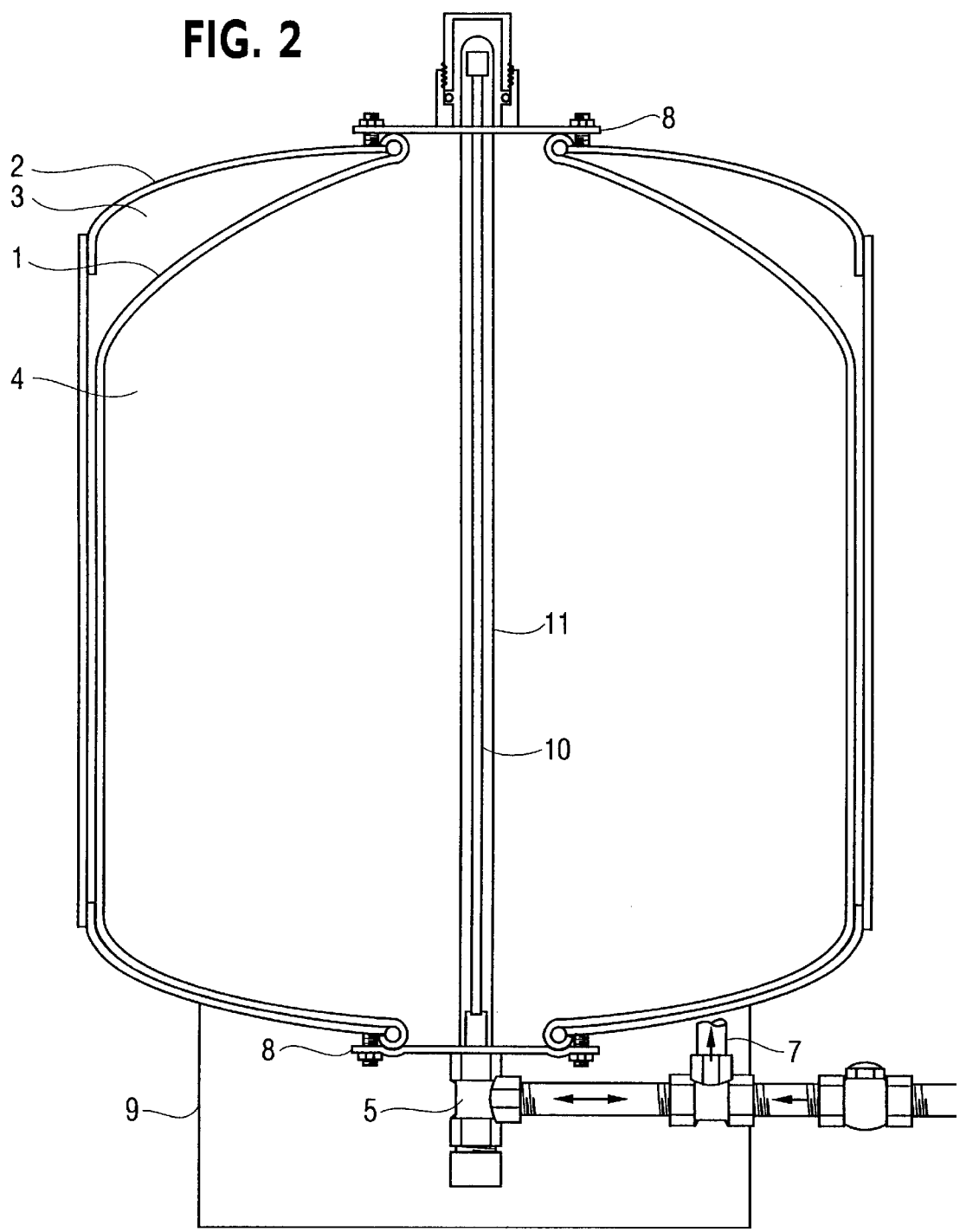
FIG. 2 shows a liquid storage and dispensing container according to a first embodiment of the invention, along with an access flange.
Figure 3:
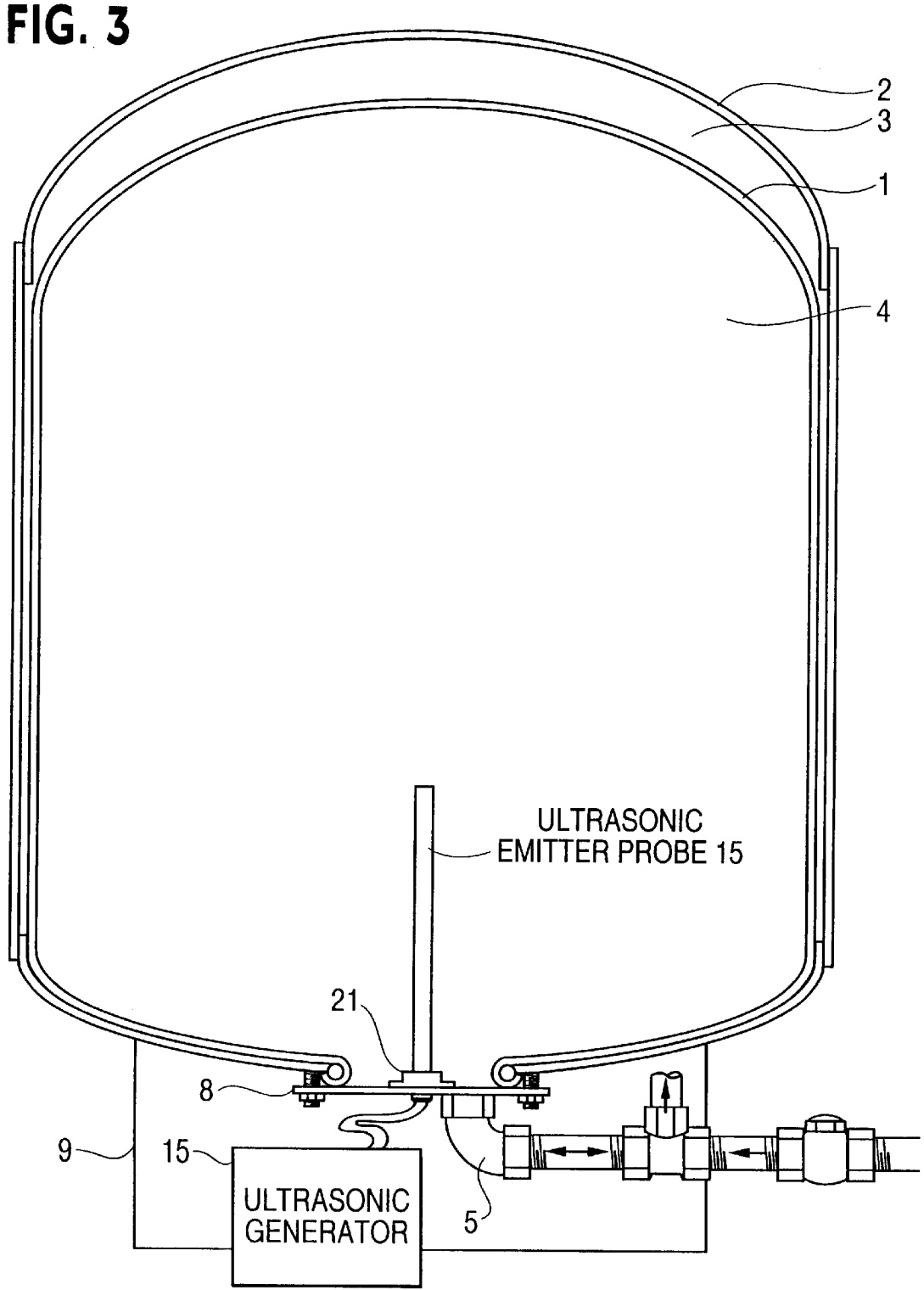
FIG. 3 shows a liquid storage and dispensing container according to a second embodiment of the invention, using an ultrasonic probe.
Figure 4:
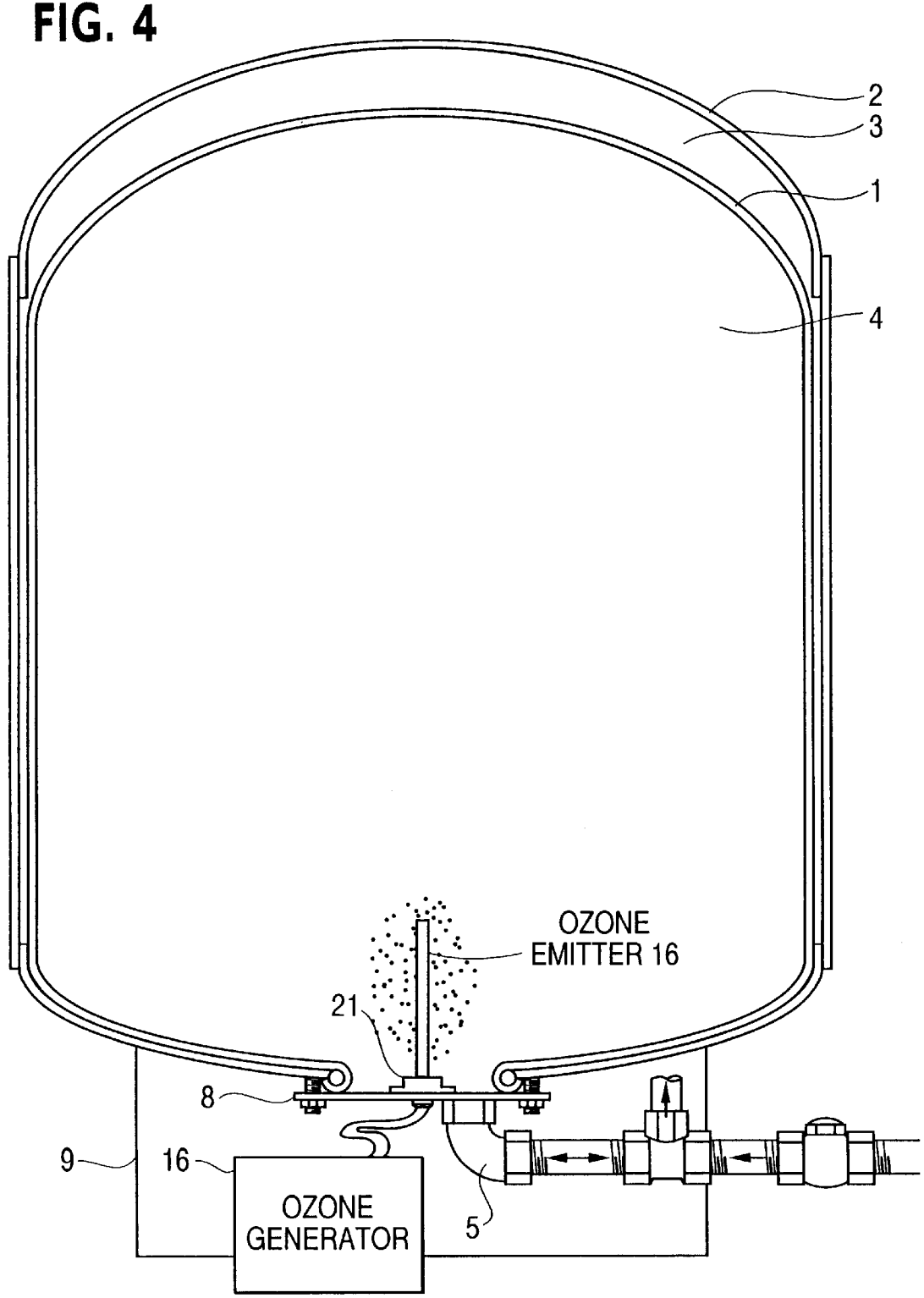
FIG. 4 shows a liquid storage and dispensing container according to a third embodiment of the invention, using an ozone emitter.
Figure 5:
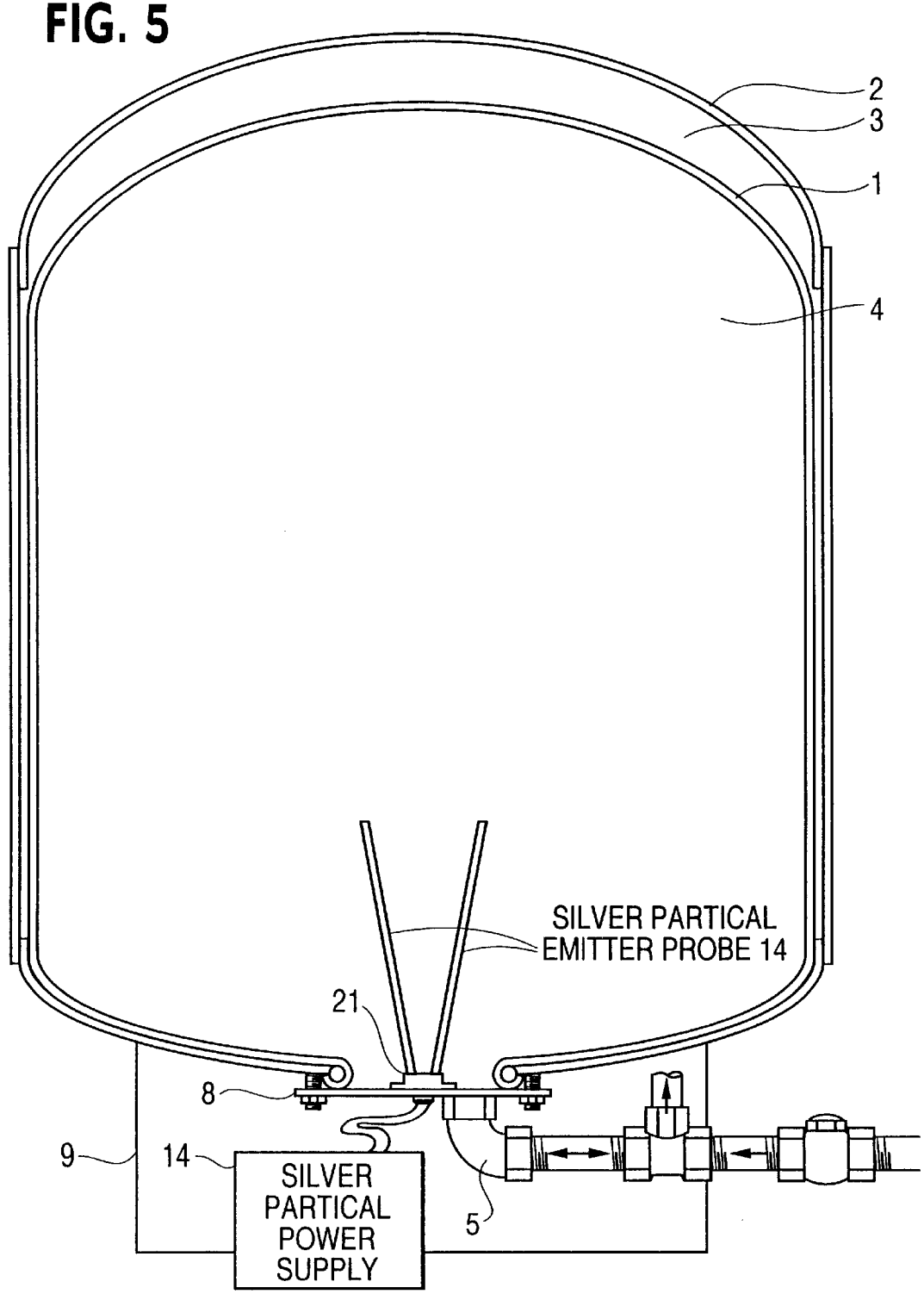
FIG. 5 shows a liquid storage and dispensing container according to a fourth embodiment of the invention, using a silver particle emitter.
Figure 6:
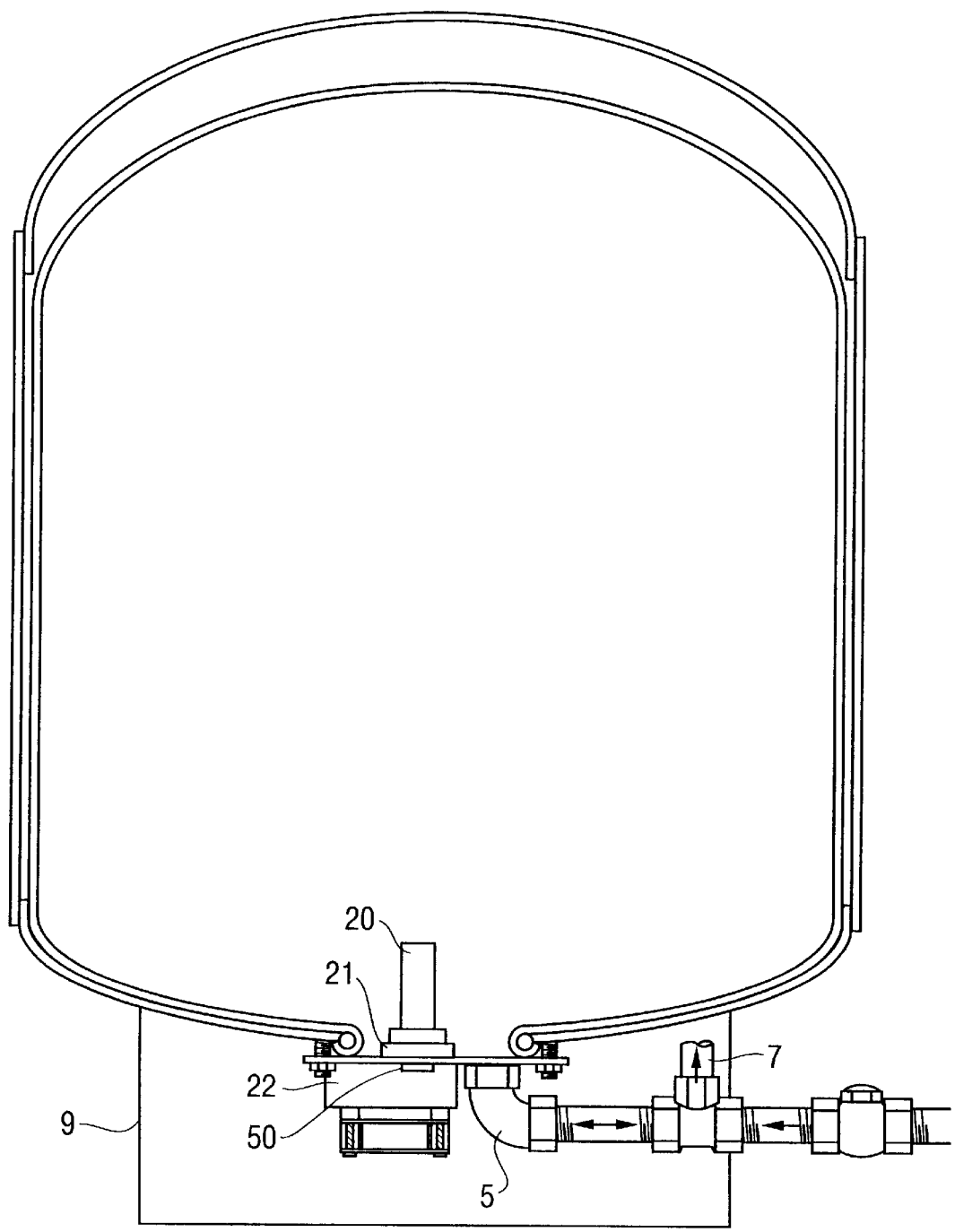
FIG. 6 shows a liquid storage and dispensing container according to a fifth embodiment of the invention, using a thermoelectric temperature adjustment unit.
Figure 7:
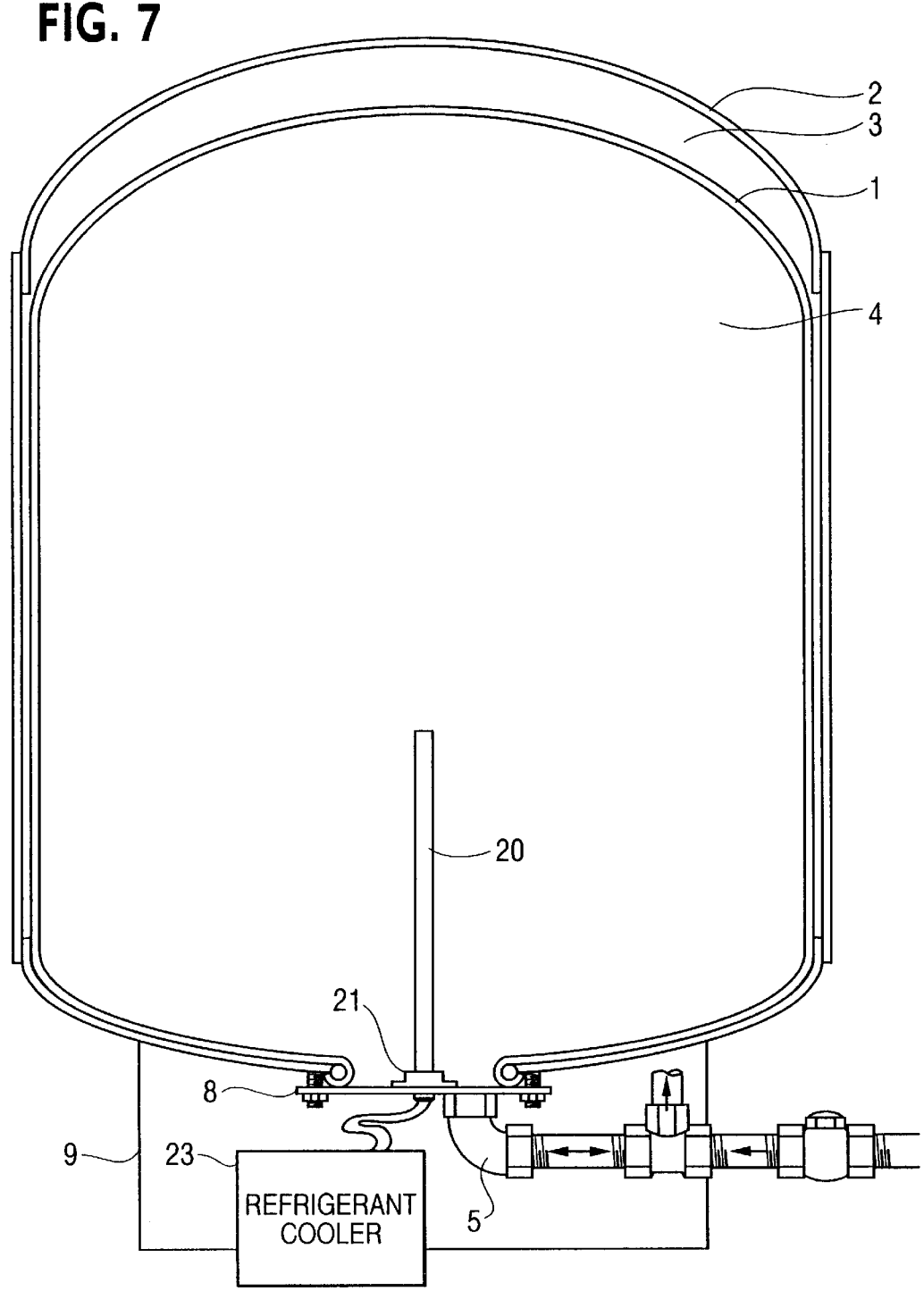
FIG. 7 shows a liquid storage and dispensing container according to a liquid storage and dispensing container according to a sixth embodiment of the invention, using a conventional temperature adjustment unit.
Figure 8:
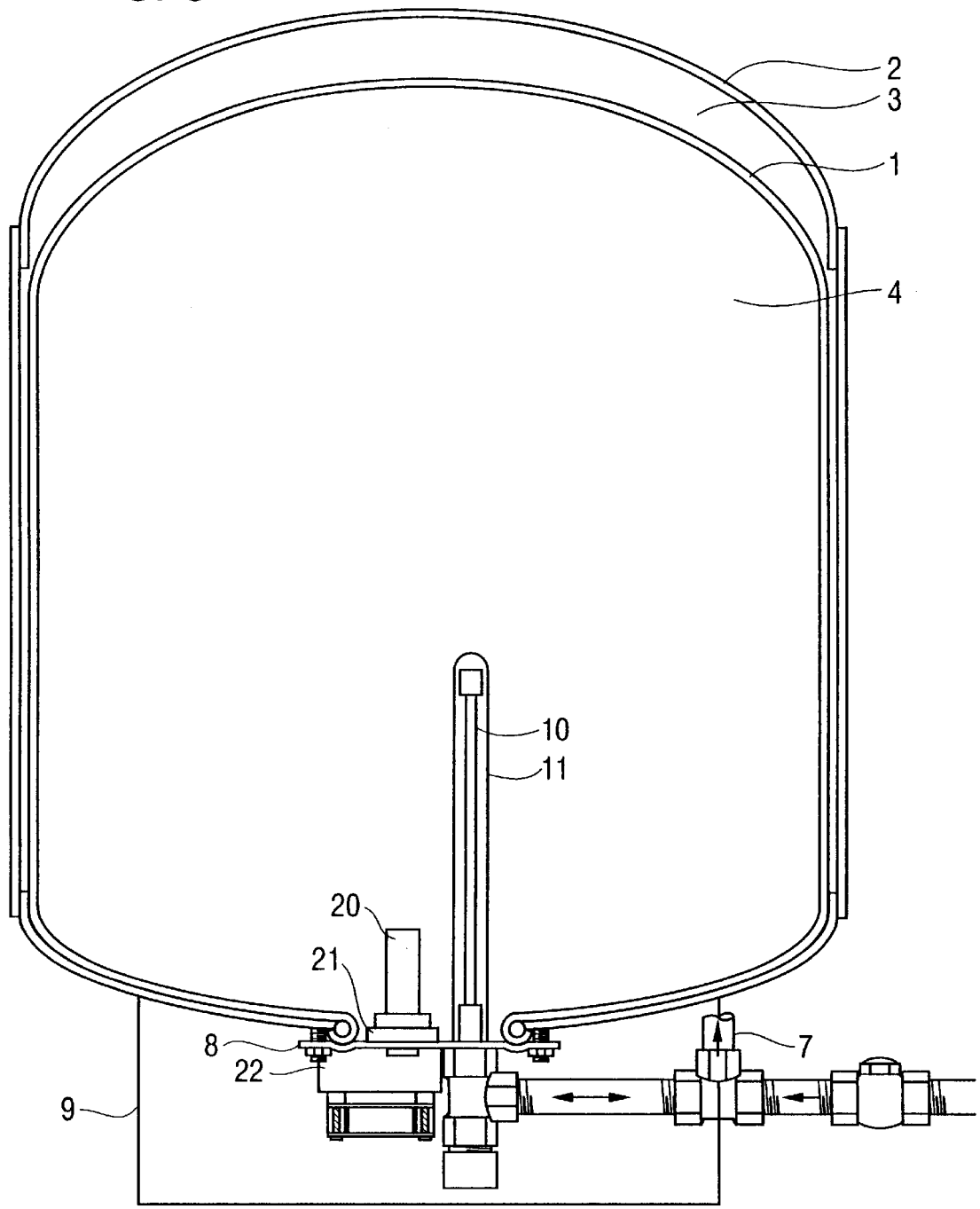
FIG. 8 shows a liquid storage and dispensing container according to a seventh embodiment of the invention, using both a sterilizer and a temperature adjustment unit.
Figure 9:
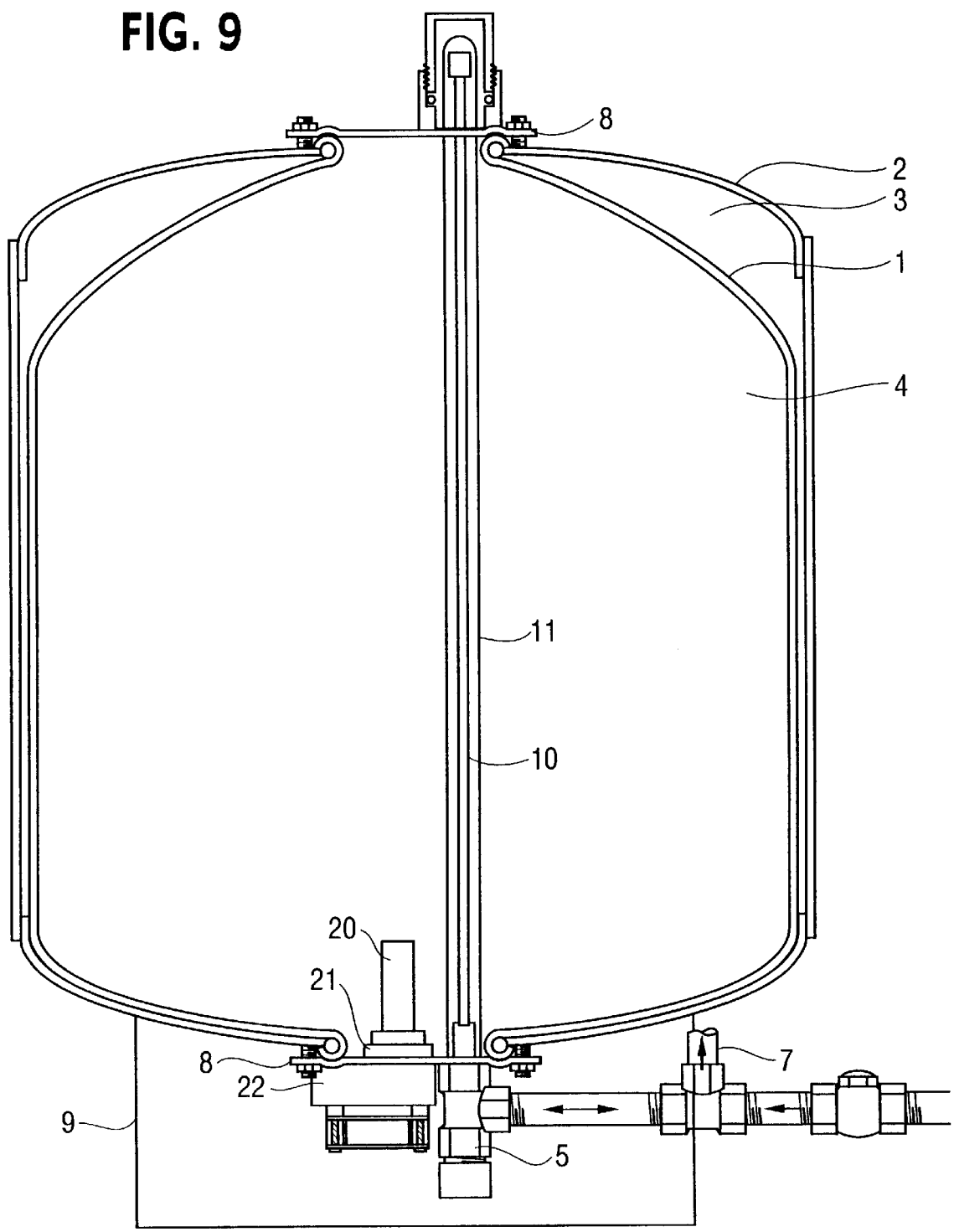
FIG. 9 shows a liquid storage and dispensing container according to the seventh embodiment of the invention, along with an access flange.
Figure 10:
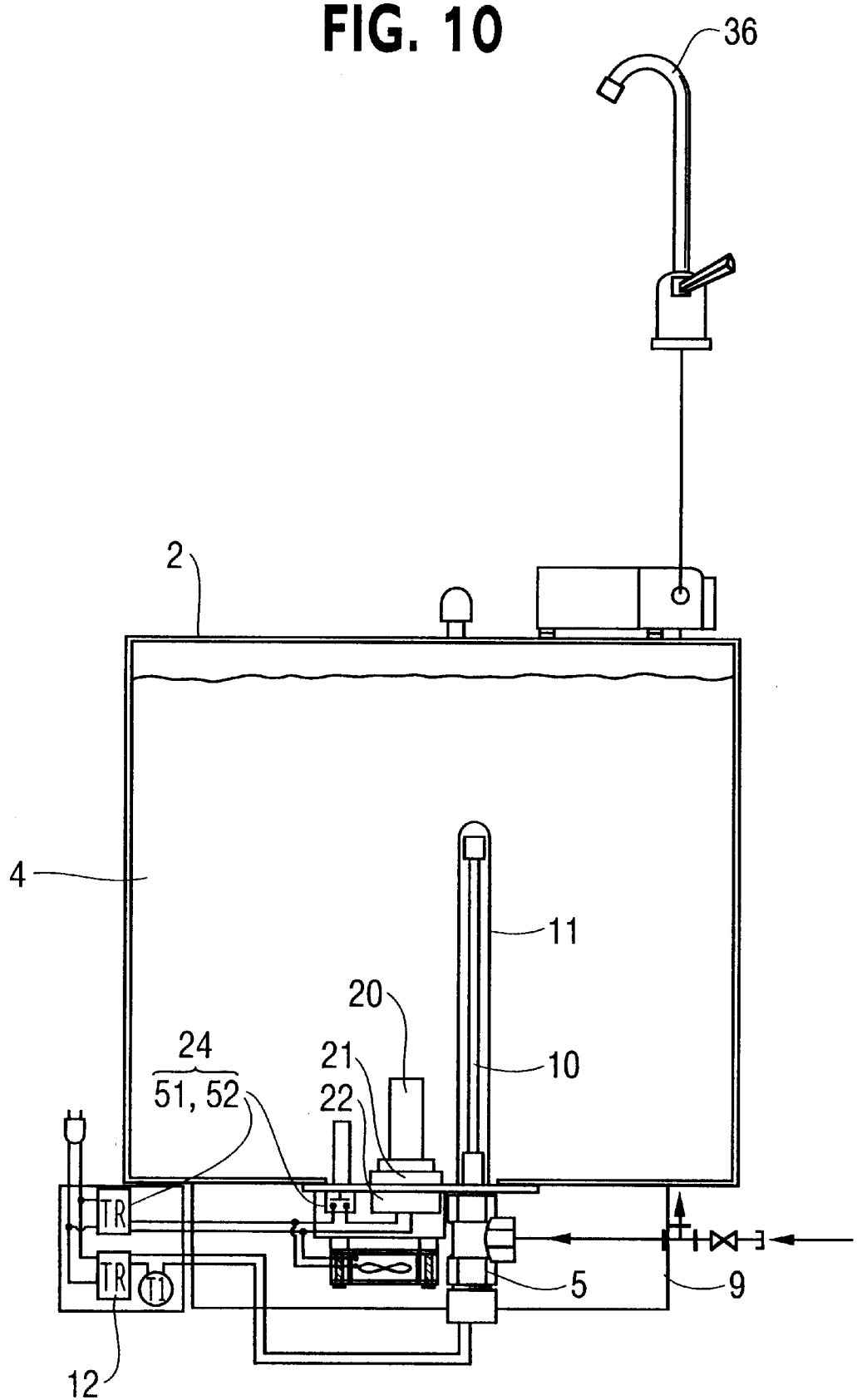
FIG. 10 shows a liquid storage and dispensing container according to an eighth embodiment of the invention, along with a power supply and a dispenser.
Figure 11:
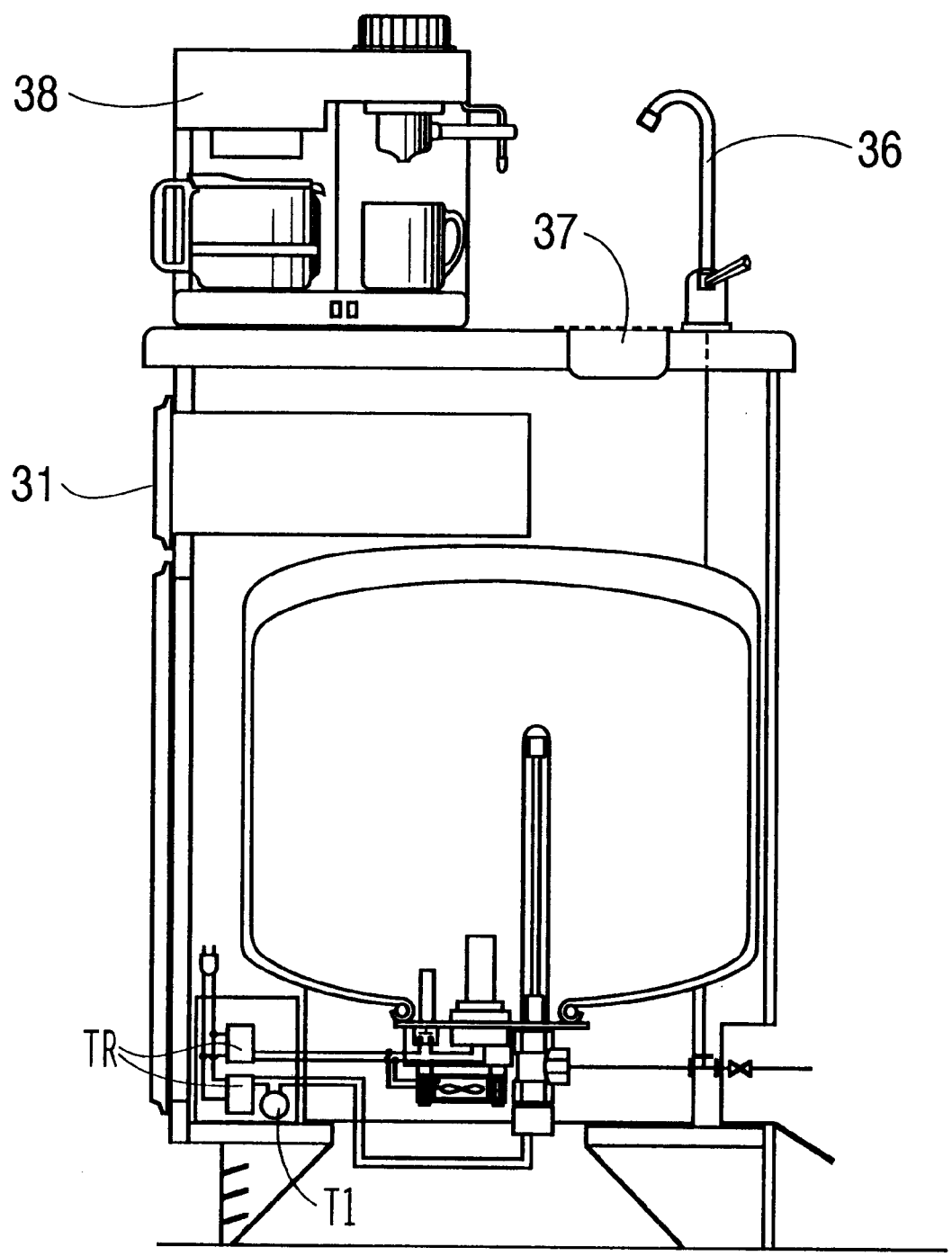
FIG. 11 shows a liquid storage and dispensing container according to a ninth embodiment of the invention, used in a cabinet having drawers, a dispenser, an end user, and a catch basin.
Figure 12:
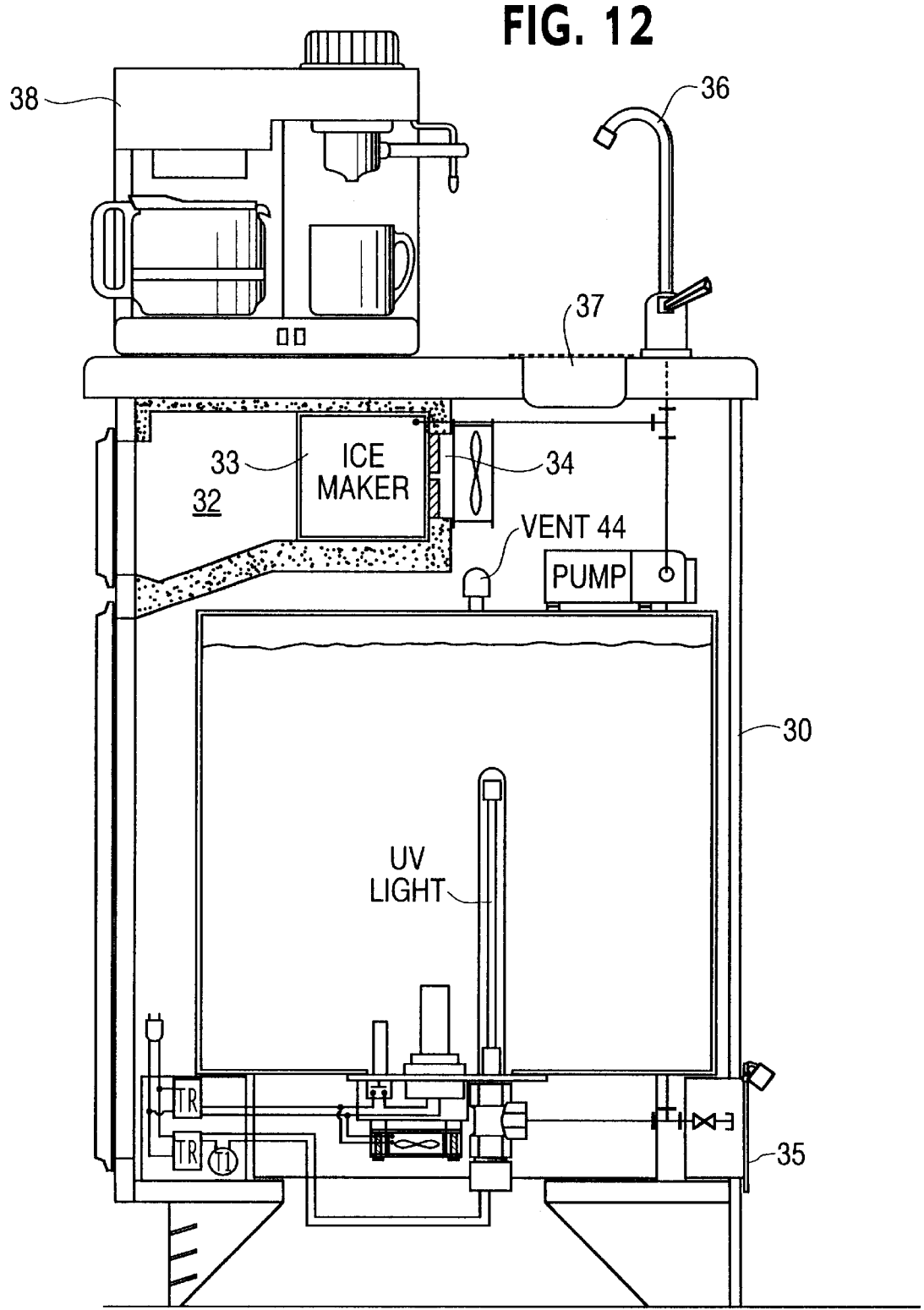
FIG. 12 shows a liquid storage and dispensing container according to the ninth embodiment of the invention, having an access door, a filtered vent, and an ice maker.
Figure 13:
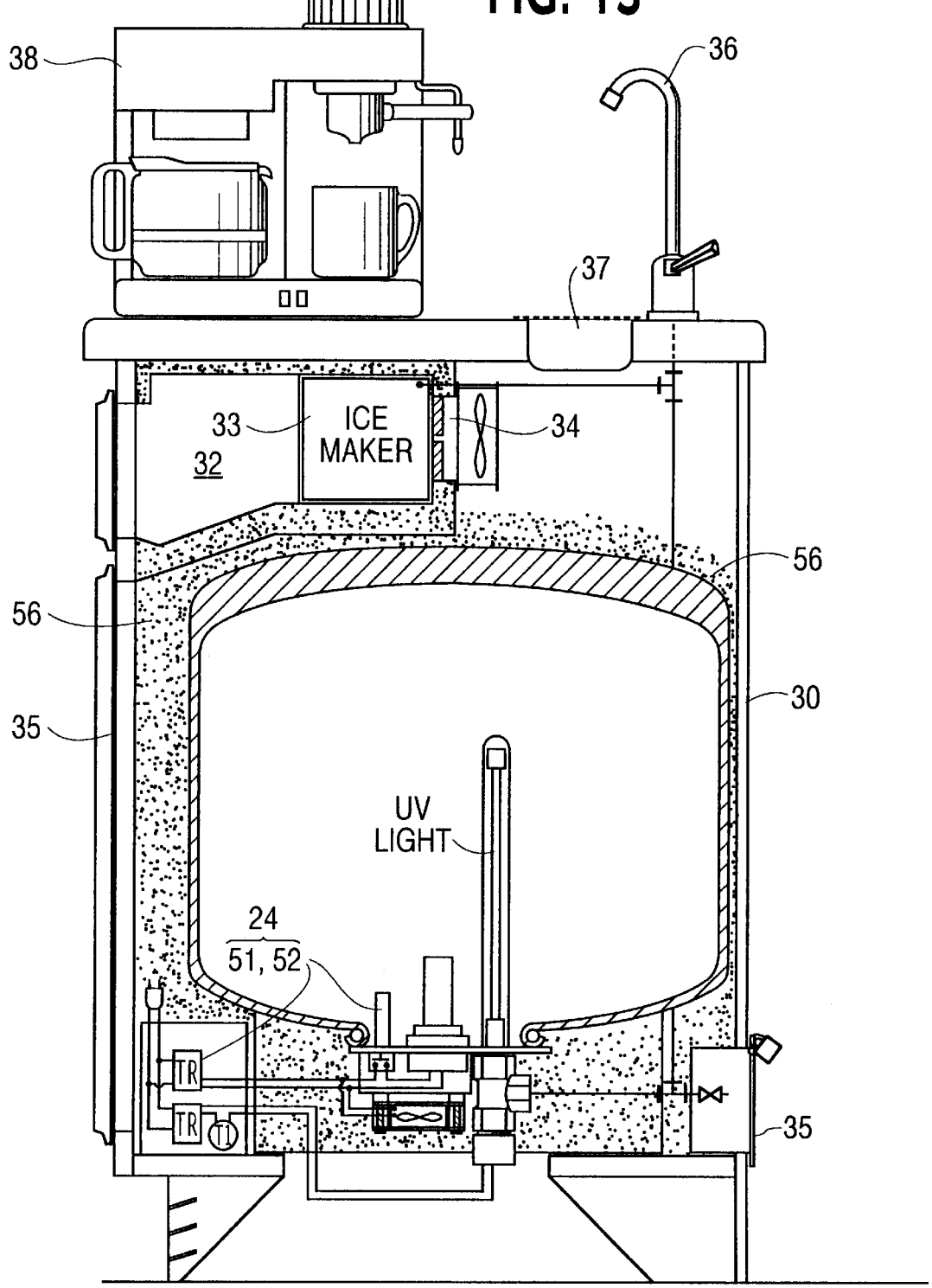
FIG. 13 shows a liquid storage and dispensing container according to a tenth embodiment of the invention, using a pressurized tank.
Figure 14:
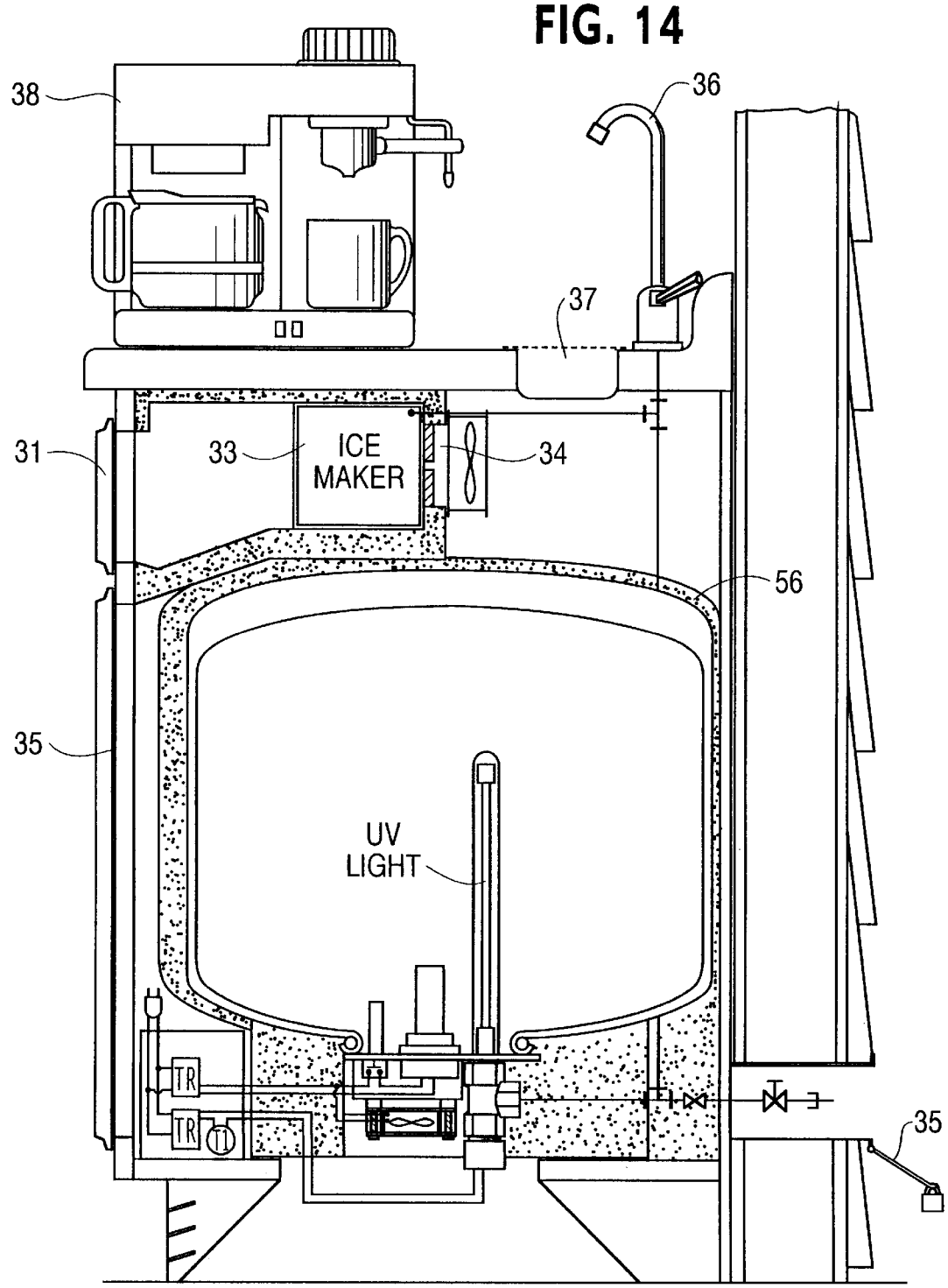
FIG. 14 shows a liquid storage and dispensing container according to the tenth embodiment, with the access door opened.
Figure 15:
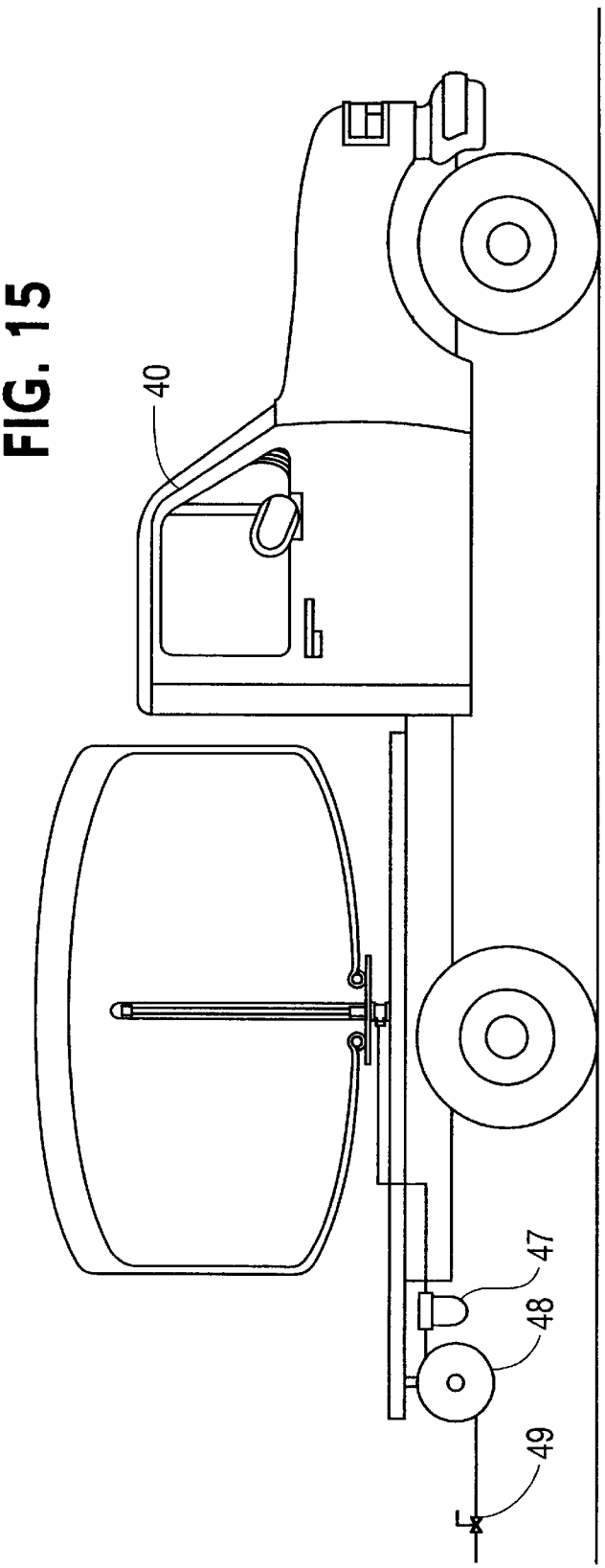
FIG. 15 shows a liquid storage and dispensing container according to part of an eleventh embodiment of the invention, towed on a delivery truck.
Figure 16:
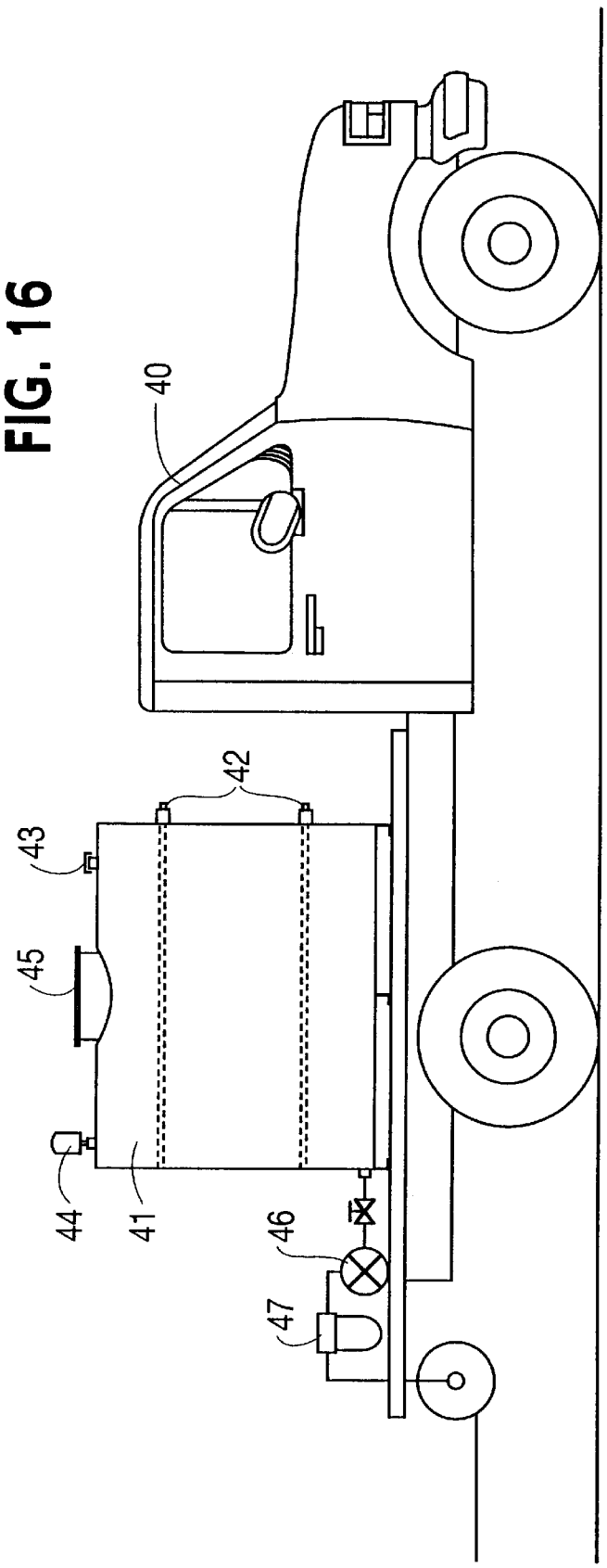
FIG. 16 shows a liquid storage and dispensing container according to part of a twelfth embodiment of the invention, with an atmospheric tank towed on a delivery truck.
Figure 17:
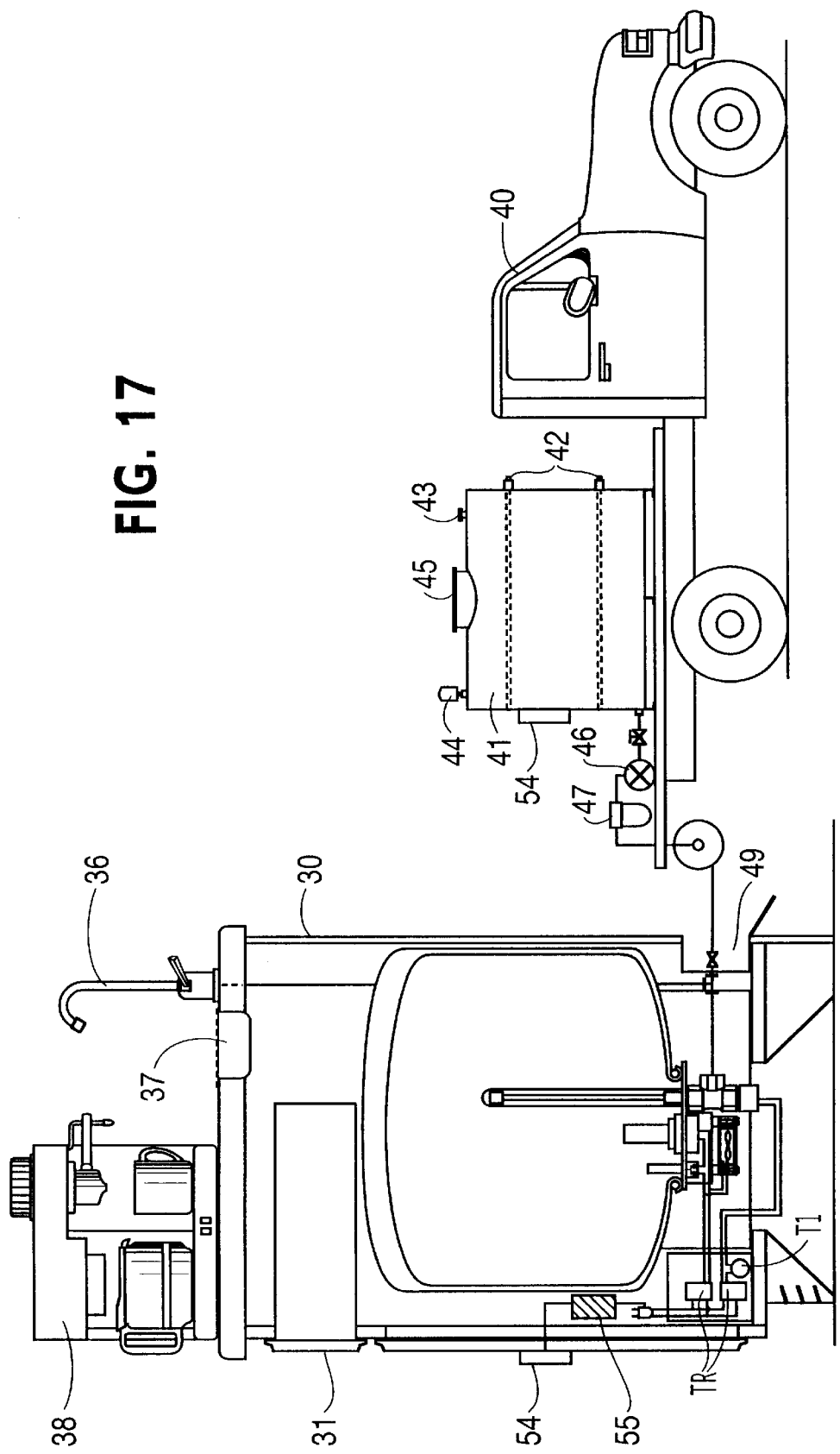
FIG. 17 shows a liquid storage and dispensing container according to the twelfth embodiment of the invention.
Figure 18:
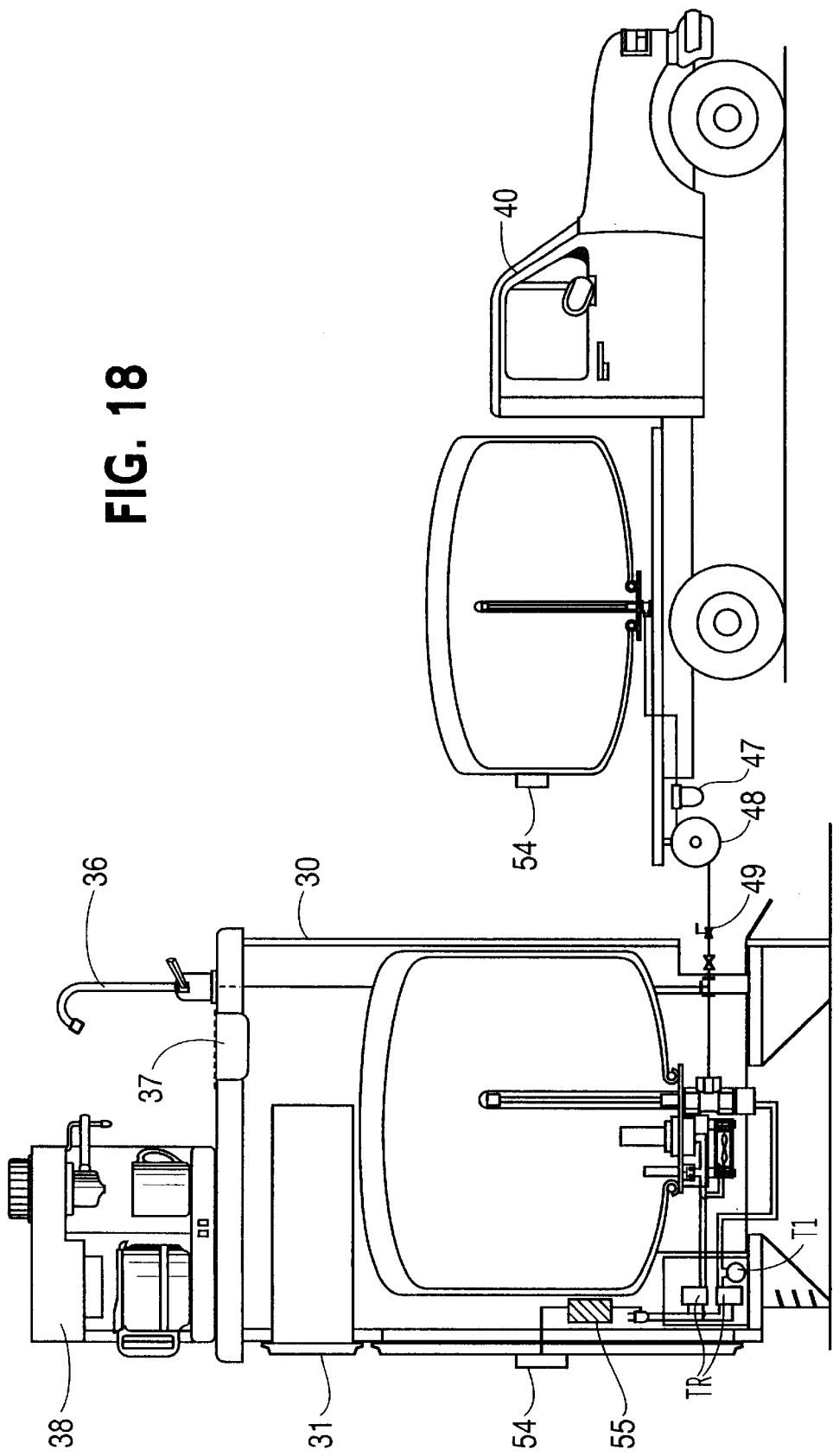
FIG. 18 shows a liquid storage and dispensing container according to the eleventh embodiment of the invention.

The above described needs are met by a liquid storage and dispensing container, which includes a tank 1, made of a flexible material. The tank 1 may be a bladder that is of food grade, and may be very elastic, formed according to the amount of liquid 4 that occupies the bladder. The container 2 actually surrounds the tank 1, and may be a hard outer shell that is pressure coded. An insulation layer 56 for reducing thermal transfer between the liquid 4 and the surroundings of the container 2 may be placed around the tank 1. In a preferred embodiment of the invention, a cavity 3 is formed between the bladder 1 and the outer shell 2. The cavity 3 is filled with air or other compressible gases which provide pressure as the bladder 1 is filled with liquid 4 by way of a bladder orifice fitting 5 through a filling receptacle, thus reducing the cavity area 3. The pressure in the cavity 3 is thus exerted on the bladder 1, so the liquid 4 in the bladder 1 is stored under pressure. Also in a preferred embodiment of the invention, the liquid 4 is a potable liquid such as drinking water or another beverage.

A liquid disperser such as a discharge fitting 7 is provided as a conduit by which liquid may flow out of the tank 1. All parts and devices that require access to the internals of the container 2 or tank 1 can have such access through one or more container flanges 8. The container 2 may rest on a container base 9 which stabilizes the container 2 as it may become extremely heavy when large amounts of liquid 4 are stored therein.

A liquid sterilizer that maintains the liquid in a sterile state in the container is provided in connection with the tank 2. In a preferred embodiment of the invention, a sterilizing light 10 is used to sterilize the liquid of bacteria and germs. In a most preferred embodiment of the invention, an ultraviolet germicidal lamp 10 that operates in the 180 nm to 450 nm wave length range is used to sterilize the liquid 4. In an even more preferred embodiment, the ultraviolet lamp 10 operates in the 240 nm to 300 nm wave length range, so that the liquid 4 in the tank 2 can be any potable liquid such as drinking water or any other beverage.

When an ultraviolet germicidal lamp 10 is used as a sterilizer, a quartz sleeve 11 is used to envelope the germicidal lamp 10 in order to isolate it from the liquid 4. Also, a UV transformer 12 is provided with a wiring harness, to power the ultraviolet light. A device T1 such as a timer may be connected with the UV transformer 12, which automatically begins and ends operation of the germicidal lamp 10 or any other sterilizer. Any sealing mechanism 13 known in the art can be used to isolate the liquid 4 from the sterilizing light unit 10.

In another embodiment, the sterilizer is a silver particle sterilizer 14. In that embodiment, silver probes are set up, and use electrolysis techniques to provide silver particles which kill bacteria in the liquid 4.

In yet another embodiment, the sterilizer is an ultrasonic sterilizer. In that embodiment, ultrasonic probes 15 are inserted into the tank 1, contacting the liquid 4, and are equipped with an ultrasonic generator.

In a further embodiment, the sterilizer is an ozone generator 16, and includes an injection mechanism which allows ozone to sufficiently contact the liquid 4 in the tank 1.

At least one cooling and heating component 20 may be attached to the container 2. The cooling component may be electrically powered, and automatically controlled using a power supply 24 which includes a transformer, wiring harness, temperature sensors, controls, etc. In a preferred embodiment, the cooling component is a thermoelectric device 22 or peltier cooler, which is a semiconductor based electronic component that functions as a small heat pump. A cooling probe 20 is part of the thermoelectric device 22, and is inserted into the tank 1, and conductively cools or heats the liquid 4. A probe seal 21 seals and retains the probe securely in place while keeping liquid 4 from leaking out of the tank 1.

As just mentioned a temperature sensor 51 may be included, and connected with the power supply 24 by a switching circuit 52. The thermoelectric device 22 may provide heat to the liquid 4 when the switching circuit 52 connected to the thermoelectric device 22 is positioned in a first state, and the device 22 may also cool the liquid 4 when the switching circuit 52 is positioned in a second state.

In a preferred embodiment of the invention, the tank 1 and the sterilization system and heating and cooling system, along with the plumbing and electrical power supply and controls are enclosed within a cabinet 30. A drawer 31 may be built into the cabinet 30 for storage space. An ice storage compartment 32 may be enclosed by the cabinet 30 as well as an ice maker 33, powered by a thermoelectric device 34. Access to the tank 1 and other accessories may be provided by an access door 35 on the cabinet 30. A valved faucet 36 or other dispenser may be attached to the tank 1 by the discharge fitting 7 to dispense liquid 4 from the tank 1. A catch basin 37 may also be included to catch spilled liquid. Other facilities such as a source of drinking water use 38, i.e.

a coffee maker, tea, cappuccino, soup, dehydrated foods, etc. may be included as an attachment to the cabinet 30.

In addition to the above cabinet system, or as an alternate to such, a delivery truck or other trucking system 40 may be used in conjunction with the tank 1 and the above described components. In such a case, a container such as an atmospheric delivery tank 41 may be mounted on the delivery truck 40. A sterilizer 42, which may be any of those used in the above embodiments, i.e. ultraviolet light, silver particle, ultrasonic, ozone, etc., is mounted on the truck 40 or directly on the container 41. A fill line 43 is provided to fill the tank, and a filtered vent 44 may be used if an atmospheric tank 41 is used as a container. The vent 44 is a source for air to enter and exit the atmospheric tank, while filtering the air at a micron level. A manway 45 may provide access to enter the atmospheric tank 41 if needed.

If both the trucking system is used, and the smaller portable system, the atmospheric tank 41 can provide a large volume of liquid to the tank 1. In such an embodiment, a pump 46 delivers liquid 4 from the delivery truck tank 41 to the customer bladder storage tank 1 or the like, through a delivery hose 49. The delivery hose 49 is held by a hose reel 48. As liquid transfers through the delivery hose 49, it is filtered using a final sub-micron filter 47.

An alarm 54 which serves as both a detector and warning device upon an event of a container malfunction and upon an event of a container defect may be added to either the container 2 or the delivery truck tank 41. Computer hardware and software 55 may be used to monitor and operate the alarm 54. Numerous types of malfunctions or defects can be detected and thereby set off the alarm 54, such as leaks, sudden pressure changes or irregularities, temperature range deviations, contaminant particulate count out of acceptable ranges, and power deficiencies or irregularities, to name a few.

Having described an embodiment of the invention, it is to be understood that the invention is not limited to any of the precise embodiments described herein. Various changes and modifications could be effected by one skilled in the art without departing from the spirit or scope of the invention as defined in the appended claims.

What is claimed is:

1. A liquid storage and dispensing container, which comprises:
   a bladder tank, made of a flexible material, for storing and dispensing said liquid;
   liquid dispersing means, connected to said bladder tank; and
   means for sterilizing said liquid while stored in said bladder tank, and maintaining said liquid in a sterile state, wherein said means for sterilizing said liquid is disposed within said bladder tank.

2. A liquid storage and dispensing container according to claim 1, wherein said sterilizing means comprises an ultraviolet light.

3. A liquid storage and dispensing container according to claim 1, wherein said sterilizing means comprises an ultrasonic generator.

4. A liquid storage and dispensing container according to claim 1, wherein said sterilizing means comprises a silver particle sterilizer.

5. A liquid storage and dispensing container according to claim 1, wherein said sterilizing means comprises an ozone generator and injection mechanism.

6. A liquid storage and dispensing container according to claim 1, further comprising at least one thermoelectric component, attached to said container.

7. A liquid storage and dispensing container according to claim 2, further comprising at least one thermoelectric component, attached to said container.

8. A liquid storage and dispensing container according to claim 6, wherein said thermoelectric component includes a cooling probe that is contained inside said tank.

9. A liquid storage and dispensing container according to claim 6, wherein said liquid is stored and dispensed under pressure, and is cooled by said thermoelectric component.

10. A liquid storage and dispensing container according to claim 6, wherein said liquid is stored and dispensed under pressure, and is heated by said thermoelectric component.

11. A liquid storage and dispensing container according to any of claim 1, further comprising a pressure sensor, indicating a quantity of said liquid in said tank.

12. A liquid storage and dispensing container according to claim 1, further comprising means for automatically beginning and ending operation of said sterilization unit.

13. A liquid storage and dispensing container according to claim 12, wherein said means for automatically beginning and ending operation is a timer providing automation of an ultraviolet light.

14. A liquid storage and dispensing container according to claim 6, further comprising means for automatically beginning and ending operation of said thermoelectric device.

15. A liquid storage and dispensing container according to claim 14, wherein said means for automatically beginning and ending operation of said thermoelectric device is a temperature sensor.

16. A liquid storage and dispensing container according to claim 6, wherein said thermoelectric device provides heat to said liquid when a switching circuit connected to said thermoelectric device is positioned in a first state, and provides cooling to said liquid when said switching circuit is positioned in a second state.

17. A liquid storage and dispensing container according to claim 1, further comprising an insulation layer for reducing thermal transfer between said liquid in said tank and a surrounding environment.

18. A liquid storage and dispensing container according to claim 1, further comprising a protective outer cover surrounding said tank, and a pressure generating means that exerts pressure in the space between said outer cover and said tank.

19. A liquid storage and dispensing container according to claim 1, further comprising work surfaces, shelves, and storage areas in the surroundings of said container.

20. A liquid storage and dispensing container according to claim 1, further comprising alarm means for detecting and alarming upon an event of a container malfunction and upon an event of a container defect.

21. A liquid storage and dispensing container according to claim 20, further comprising computer hardware and software used to monitor and operate said alarm means.

22. A liquid storage and dispensing container according to claim 1, wherein said liquid is potable.

* * * * *